United States Patent [19]

Carter

[11] Patent Number: 4,713,049
[45] Date of Patent: Dec. 15, 1987

[54] URETERAL STENT KIT

[75] Inventor: Garry L. Carter, Racine, Wis.

[73] Assignee: Medical Engineering Corporation, Racine, Wis.

[21] Appl. No.: 893,381

[22] Filed: Aug. 5, 1986

[51] Int. Cl.⁴ .......................................... A61M 25/00
[52] U.S. Cl. ........................................ 604/8; 604/95; 604/282
[58] Field of Search ................. 604/95, 8–10, 604/170, 281; 128/657–658, 341, 348.1, 772

[56] References Cited

U.S. PATENT DOCUMENTS

| | | | |
|---|---|---|---|
| 229,633 | 7/1880 | Ptarre | 128/341 |
| 3,757,768 | 9/1973 | Kline | 607/170 X |
| 4,212,304 | 7/1980 | Finney | 128/349 R |
| 4,307,723 | 12/1981 | Finney | 128/349 R |
| 4,531,933 | 7/1985 | Norton et al. | 604/8 |
| 4,610,657 | 9/1986 | Densow | 604/8 |
| 4,671,795 | 6/1987 | Mulchin | 604/8 X |

OTHER PUBLICATIONS

Radiology 136:220–231, Jul. 1980.

Primary Examiner—Dalton L. Truluck
Attorney, Agent, or Firm—Quarles & Brady

[57] ABSTRACT

A ureteral stent kit for inserting a ureteral stent and bypassing obstructions in the ureter comprises an elongated, flexible tubular stent which has a lumen and at least one end set in the form of a hook, a removable tubular guide member sized to fit in the lumen in the stent and having a flexible forgiving tip and a relatively stiff, removable core which is sized to fit within the lumen of guide member and to support the forgiving tip.

4 Claims, 5 Drawing Figures

U.S. Patent   Dec. 15, 1987   Sheet 1 of 2   4,713,049
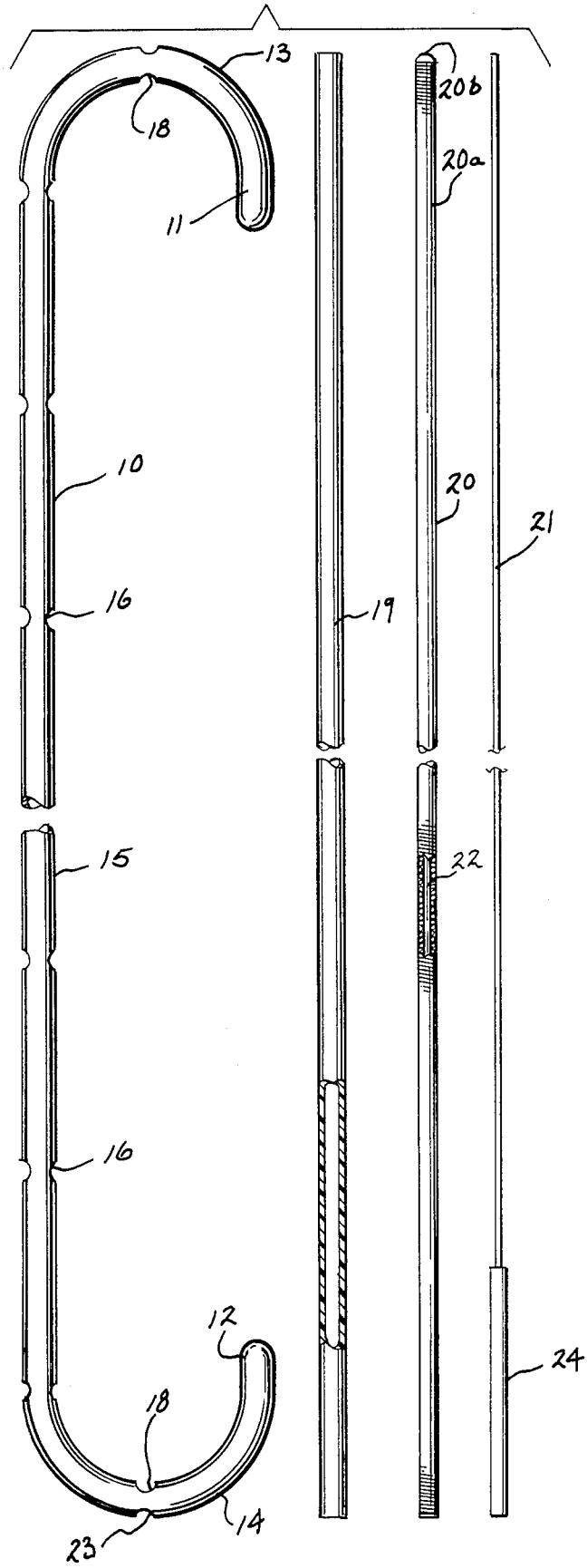
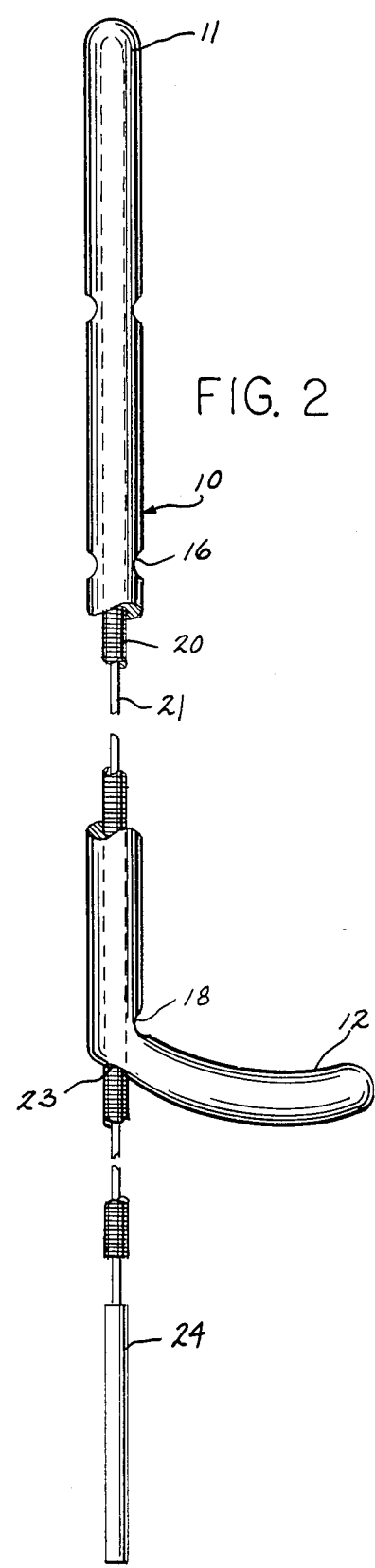

URETERAL STENT KIT

FIELD OF THE INVENTION

The present invention relates generally to ureteral stents. More particularly, it relates to a ureteral stent kit which includes a two piece quide wire system which can be used to maneuver a stent past obstructions.

BACKGROUND OF THE INVENTION

Indwelling ureteral catheter stents or drainage tubes have been used to bypass ureteral obstructions or uretero-vaginal fistulas and to achieve and to maintain urinary drainage. In the past, stents made of straight lengths of open end tubing have been used for this purpose and have provided good drainage for sustained periods of time. However, the use of such open end tubing has not been completely satisfactory. For example, in some instances, the tubing has migrated and in others it has been expelled.

Various attempts have been made to produce stents which do not have the problems which accompany the use of such tubing. For example, stents have been designed which are closed at one end to facilitate passage into a body passage and which have at the other end a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder.

In U.S. Pat. No. 4,212,304 issued July 15, 1979 and U.S. Pat. No. 4,307,723 issued Dec. 29, 1981, ureteral stents are disclosed which have hooks at each end which are surprisingly effective in preventing migration and expulsion. The patented stents are widely accepted because they can be easily introduced both endoscopically and during open surgery. However like most other commercially available stents it is difficult to maneuver them past obstructions in the ureter.

SUMMARY OF THE INVENTION

It is an object of the present invention to disclose a kit containing a ureteral stent, which is soft and flexible enough for patient comfort, and a two piece guide wire system which can be used to maneuver the stent past obstructions in the ureter.

It is another object to disclose a method of bypassing an obstruction in the ureter using the stent and guide wire system of the present invention.

The kit of the present invention comprises an elongated, flexible, tubular stent of substantially uniform outside surface throughout its length having proximal and distal ends which are set in the form of hooks. The kit also includes a novel guide wire system comprising a tubular flexible tip guide member and a removable core.

The stent is preferably made of a soft, flexible, radiopaque material and the proximal and distal ends are closed. The preferred stent is provided with indicating means which can be seen through a cystoscope to show the direction the proximal hook will extend when the stent is in place.

The guide wire system of the present invention comprises a relatively flexible, tubular, guide member and a more rigid removable core which is sized to fit and move freely in the lumen of the guide member. The tubular guide member has at least a portion adjacent the leading end which is more flexible than the leading end of the core.

The stent is normally inserted in the ureter by placing the guide member and its removable core into the lumen of the stent through an opening at the distal end. The guide member and core are advanced until the leading ends of the guide member and the core both reach the closed proximal end of the stent. Because the removable core is relatively stiff the proximal hook is straightened in the process. Next, a stent pusher is threaded over the free ends of the guide member and the removable core behind the stent to aid the passage of the stent through a cystoscope into the ureter.

In the event that an obstruction in the ureter is encountered which prevents the stent from being inserted in the renal pelvis or lower calix in the normal manner, the removable core is retracted so that only the flexible leading end of the guide member supports the stent. The flexible leading end of the tubular guide member and the proximal end of the stent are then maneuvered past the obstruction. Once past the obstruction the core is again advanced in the guide member and the stent positioned in the lower calix or renal pelvis in the normal manner. The guide member and the movable core are then withdrawn and the stent pusher disengaged, if necessary, from the stent.

The above stated and other objects and advantages of the invention will be apparent from the description which follows:

DESCRIPTION OF THE DRAWINGS

FIG. 1 is an elevational view of the preferred embodiment of the kit which includes a stent, a stent pusher, the guide member and the removable core;

FIG. 2 is an elevational view showing the guide member and the core in the lumen of the stent and the proximal hook straightened;

DESCRIPTION OF THE PREFERRED EMBODIMENT

Figure 3:
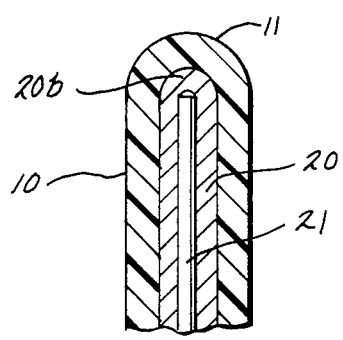
FIG. 3 is an enlarged sectional view of the proximal end of the stent, showing the leading ends of the removable core and the guide wire member seated against the closed end of the lumen in the proximal end of the stent.

In the preferred embodiment shown in FIG. 1, the stent kit includes a stent 10 which is an elongated tubular member having a proximal end 11 and a distal end 12. Portions adjacent each of the ends 11 and 12 of the stent 10 are formed and set in the shape of gently curved hooks 13 and 14. Both the proximal end 11 and the distal end 12 as shown are closed. However, it may be preferred to supply the stent 10 with the distal end 12 open to receive guide wire system to be described. The proximal end 11 can also be open provided the opening is small and does not interfere with the function of the guide means.

The two gently formed opposed hooks 13, 14 at the ends 11 and 12 of the stent prevent it from migrating either upwardly or downwardly once it is in place. The hooks 13 and 14 preferably extend in opposite directions so that when the stent 10 is used as an indwelling ureteral stent the proximal end 11 can hook into the lower calix or renal pelvis while the distal end 12 curves out into the bladder. This design also prevents the tip of the stent from impinging directly into the bladder mucosa thereby decreasing discomfort and inflammation.

The stent 10 includes a relatively straight intermediate section 15 which extends between the proximal hook 13 and the distal hook 14.

Referring now to FIGS. 1, 2, 4 and 5 it can be seen that the stent 10 has radial drainage passages 16 which connect the lumen 17 (best seen in FIG. 5) of the stent 10 to the outside and permit inside/outside drainage. The drainage passages 16 are located about 5 centimeters apart on both sides of the straight section 15. The passages 16 of both sides are preferably aligned. Returning to FIGS. 1, 4 and 6, it can be seen that there are similar openings 18 in the inside walls of the proximal hook 13 and distal hook 14.

Referring again to FIG. 1, there also can be seen a stent pusher 19, a relatively large diameter hollow guide member 20, which is sized to fit in the lumen 17 of the stent 10, and a smaller diameter core 21 which is intended to fit within the lumen 22 of the guide wire member 20.

When normal endoscopic insertion is employed, the relatively large diameter guide member 20 with the core 21 in place is introduced into the lumen 17 of the stent 10 via an opening 23 near the distal end 12 and advanced to the proximal end 11 to straighten hook 13 as seen in FIG. 2. The leading end 20a of the guide wire member 20 and the leading end 21a of the core 21 are prevented from leaving the lumen 17 of the stent 10, as seen best in FIG. 3, because of the closed proximal end 11.

To assist in properly positioning the stent 10 in the patient the stent pusher 19 may be threaded over the free end of the guide member 20 and core 21. The stent pusher 19 may then be used to advance the stent 10 into position. Once the stent 10 is properly positioned, the guide member 20, the core 21 and the stent pusher 19 are removed by withdrawing the stent pusher 19 while holding the guide member 20 and core 21 thus causing the stent 10 and stent pusher 19 to separate after which the guide member 20 and core 21 and then the stent pusher 19 are withdrawn.

Figure 4:
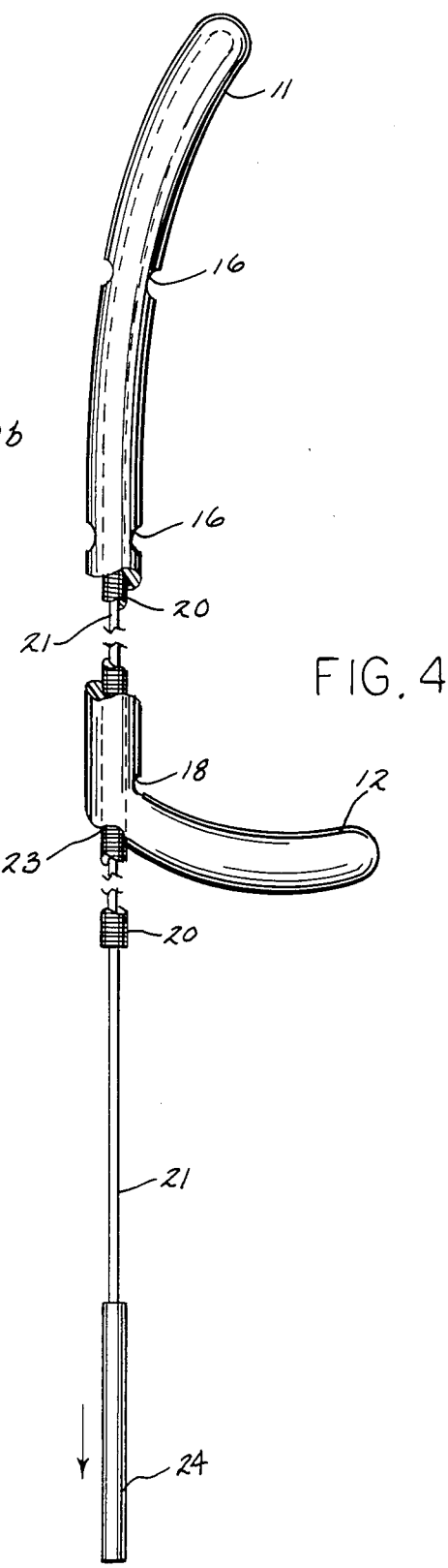
FIG. 4 is an elevational view similar to FIG. 2 but, the leading end of the removable core is partially retracted from inside the leading end of the guide member which is still in the proximal end of the stent.
Figure 5:
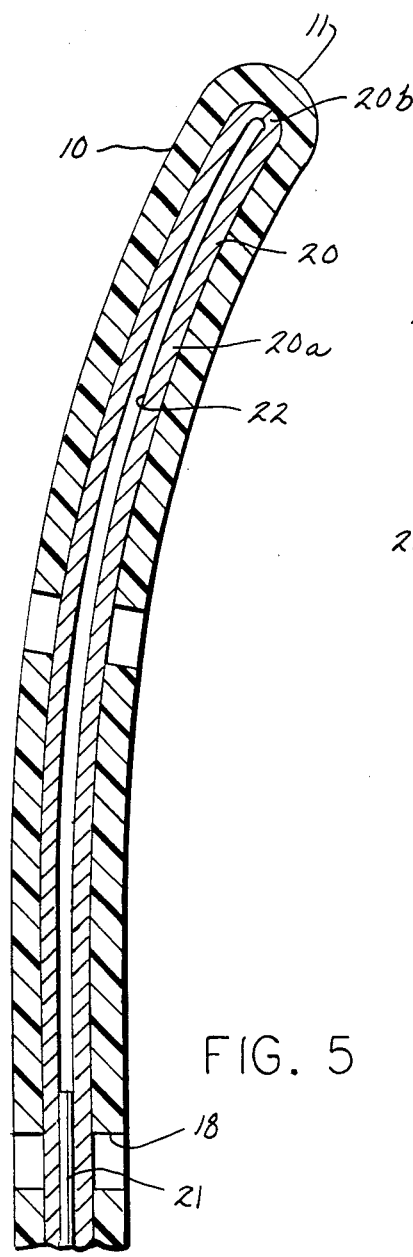
FIG. 5 is an enlarged sectional view of the proximal end of the stent of FIG. 4 showing the removable core partially retracted and the proximal end of the stent being supported by only the leading end of the guide wire member.

When an obstruction in the ureter is encountered that cannot be bypassed by the stent 10 using the normal method of introduction, the leading end 21a of core 21 is partially withdrawn so that the forgiving, unreinforced, flexible tip 20a at the proximal end of the guide member 20 is the sole support for the proximal end 11 (seen best in FIGS. 4 and 5). The proximal end 11 of the stent 10 and the forgiving, unreinforced leading end or tip 20a of the guide member 20 are then maneuvered past the obstruction in the ureter. When it is known that they are safely past the obstruction, the leading end 21a of the core 21 may be once again advanced in the guide member 20 past the obstruction to the closed end 20b of the guide member 20 to straighten the hook 13. The stent 10 can then be pushed into place as described with the stent pusher 19. The guide member 20 and core 21 are then withdrawn and the stent pusher 19 is disengaged from the stent 10.

When it is desired to replace an indwelling stent of the type shown, the stent is first cystoscopically visualized and then a foreign body forceps or a retractable type stone basket (neither shown) is advanced through the cystoscope and used to retract the stent 10 until the distal end 12 can be reached and used to withdraw the stent from the patient.

The stent 10 is made of a suitable flexible material which is soft and stiff enough for the intended purpose and which preferably contains a radiopaque material. The stent may be supplied in 7 French and 8.5 French sizes in 16, 24, 26, 28 and 30 cm lengths. The listed length of the stent 10 is the length of the section 15 and does not include the hooked ends 13 and 14. This allows the user to radiographically estimate the ureteral length and select the proper stent for passage.

The ureteral catheter stent 10 of the present invention is preferably made of nylon which has a durometer between about 70 Shore 'A' and about 55 Shore 'D' to which 10% barium sulfate has been added to the radiopaque agent. Stents made of this material have been found to be soft enough not to cause undue discomfort to the patient and stiff enough to bypass obstructions in the ureter. Other plastic materials such as silicone rubber which possess the desired properties and resist encrustation with urine salts can also be used.

The stent 10 is preferably formed by extruding a length of tubing of the desired size and durometer. The proximal end 11 and distal end 12 of the tubing are then placed in molds to close the open ends of the lumen 17. The length of tubing is then placed in a form to shape the hooks 13 and 14. The openings 16, 18 and 23 may be formed at any step of the process by piercing the wall of the tubing with a flattened, sharpened hole cutter of the desired size or by use of a laser or any other conventional means.

The guide member 20 is a tubular member having a relatively flexible forgiving leading end 20a which is closed. The preferred guide member has an OD of 0.032 inches, and ID of 0.016 inches and is formed of stainless steel.

The core 21 which is sized to fit within the tubular guide member 20 is less flexible than the guide member 20 and may be formed of stainless steel wire. It preferably has an OD of 0.013 inches. It is provided with an enlarged handle 24 at its distal end. The length of core 21 should be greater than that of the guide member 20 so that the handle 24 will protrude from the guide member 20 when the leading end 21a is seated against the closed end 20b of the guide member 20. The handle 24 is used to retract and advance the core 21.

The kit of the present invention will comprise a stent 10, a guide member 20 and a core 21. The core 21 and guide member 20 can be in place in the stent 10 or the components may be unassembled. A stent pusher 19 may be supplied as a component of the kit or a satisfactory stent pusher also may be made from a half length of a relatively stiff standard ureteral catheter, preferably 5 French. The guide system comprised of the guide member 20 and core 21 also may be sold without the stent.

In the preferred embodiment described and shown in the drawing, the proximal and distal end portions of the catheter stent are both in the form of gently curved, closed hooks. However, it is to be understood that the term "hook" is intended to include other functionally equivalent shapes such as coils which prevent migration and do not increase the effective outer diameter of the stent, or complicate its method of introduction. It also should be understood that the guide wire system of the present invention may be used with other types of ureteral stents including adjustable length stents and stents with magnetically attractable distal ends.

It will be readily apparent to those skilled in the art that a number of modifications and changes can be made without departing from the spirit of the invention. Therefore, it is to be understood that the scope of the invention is not be be limited by the foregoing description, but only by the claims.

I claim:

1. A ureteral stent kit comprises an elongated flexible tubular stent of substantially uniform outside surface throughout its length having at least one end which is set in the form of a hook, said stent having a lumen; a flexible, reinforced guide member having a relatively more flexible, unreinforced tip portion and a lumen, said member being sized to fit within the lumen of the stent; and, a removable, relatively rigid, elongated core means for the guide member, said core means being sized to freely move within the lumen of said guide member.

2. A kit for bypassing obstructions in the ureter with a ureteral stent, said kit comprising:
    (a) a ureteral stent comprising an elongated, relatively flexible, tubular member having at least one drainage opening extending through a wall thereof, said member having a lumen and at least one end set in the form of a hook;
    (b) a relatively flexible, reinforced tubular guide member, said guide member being sized to fit and move within the lumen of said stent and having a central lumen and a more flexible, unreinforced proximal end; and,
    (c) a relatively rigid, elongated core means for the guide member, said core means being sized to both fit within and move freely in the lumen of said guide member so that when the guide member and core means are within the lumen of the stent they can be advanced to straighten both hooks and if an obstruction in the ureter is encountered the core means can be partially withdrawn so that the proximal end of the stent is solely supported by the flexible, unreinforced proximal end of the guide member and can be maneuvered past the obstruction.

3. A method for inserting a ureteral stent in the ureter and for maneuvering the stent past any obstructions in the ureter which might be encountered, said method comprising:
    (a) introducing into the ureter a ureteral stent comprising an elongated, flexible, tubular member having a lumen, said member having at least one drainage passage extending through a wall thereof connecting the lumen to the outside and at least one end set in the form of a hook; said stent having in the lumen thereof a guide system comprising a tubular, flexible, reinforced guide member having a more flexible, unreinforced end and a lumen; and a relatively rigid, elongated core means for the guide member which is sized to fit within the move in the lumen of the guide member, said core means straightening said hook;
    (b) advancing said stent and guide system until an obstruction in the ureter is encountered and then partially retracting said core means from within the guide member so that the proximal end of the stent is supported solely by the unreinforced end of the guide member; and,
    (c) maneuvering the proximal end of the stent and the unreinforced end of the guide member past the obstruction.

4. A guide system for inserting a ureteral stent into a patient, said guide system comprising a relatively flexible, elongated, tubular guide member of generally uniform diameter having a lumen and being reinforced except for a minor unreinforced portion at the proximal end, and a closed proximal tip; and, an elongated relatively rigid core means, said core means being sized to fit in and move freely the entire length of the lumen of said guide member including the unreinforced portion so that the core means can be withdrawn if desired so that the relatively more flexible unreinforced portion of the proximal end of said guide member is unsupported by the core means and it can be maneuvered about an obstruction that might be encountered.

* * * * *